(12) United States Patent
Smith et al.

(10) Patent No.: US 7,212,852 B2
(45) Date of Patent: May 1, 2007

(54) BIOIMPEDANCE MEASUREMENT USING CONTROLLER-SWITCHED CURRENT INJECTION AND MULTIPLEXER SELECTED ELECTRODE CONNECTION

(75) Inventors: Kenneth Carless Smith, Toronto (CA); Joel Steven Ironstone, Toronto (CA); Frank Zhang, Scarborough (CA)

(73) Assignee: Z-Tech (Canada) Inc., Toronto (CA)

( * ) Notice: Subject to any disclaimer, the term of this patent is extended or adjusted under 35 U.S.C. 154(b) by 313 days.

(21) Appl. No.: 10/722,508

(22) Filed: Nov. 28, 2003

(65) Prior Publication Data
US 2004/0171961 A1   Sep. 2, 2004

Related U.S. Application Data

(60) Provisional application No. 60/429,316, filed on Nov. 27, 2002.

(51) Int. Cl.
*A61B 5/00* (2006.01)
(52) U.S. Cl. .................................... 600/547
(58) Field of Classification Search ............... 600/547
See application file for complete search history.

(56) References Cited

U.S. PATENT DOCUMENTS

| | | | | |
|---|---|---|---|---|
| 4,184,486 A | * | 1/1980 | Papa ........................... | 600/373 |
| 4,291,708 A | * | 9/1981 | Frei et al. .................... | 600/547 |
| 5,415,164 A | * | 5/1995 | Faupel et al. ................ | 600/372 |
| 5,919,142 A | * | 7/1999 | Boone et al. ................ | 600/547 |
| 6,584,348 B2 | * | 6/2003 | Glukhovsky ................. | 600/547 |
| 6,625,487 B2 | * | 9/2003 | Herleikson ..................... | 607/8 |
| 6,845,264 B1 | * | 1/2005 | Skladnev et al. ........... | 600/547 |
| 2002/0093992 A1 | | 7/2002 | Plangger | |

FOREIGN PATENT DOCUMENTS

| | | |
|---|---|---|
| EP | 1 146 344 | 10/2001 |
| GB | 2 131 558 | 6/1984 |
| GB | 2 260 416 | 4/1993 |

* cited by examiner

*Primary Examiner*—Max Hindenburg
(74) *Attorney, Agent, or Firm*—Bereskin & Parr

(57) ABSTRACT

A system and method for measuring a voltage in a body part are described. The system includes a multiplexing unit, and N body leads for electrically connecting the multiplexing unit to the body part. The system also includes a controller switching unit for allowing a current to flow through the body part between two body leads, $n_1$ and $n_2$ of the N body leads, and a resultant voltage to be measured between two body leads, $n_3$ and $n_4$ of the N body leads, where $n_1 \neq n_2$ and $n_3 \neq n_4$, but where $n_1$ $n_2$ $n_3$ and $n_4$ need not otherwise be distinct.

19 Claims, 8 Drawing Sheets

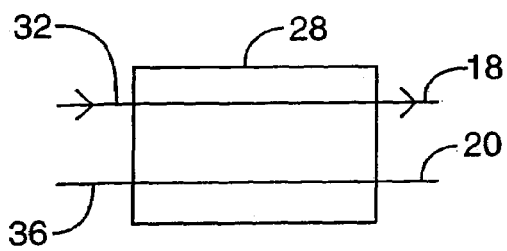
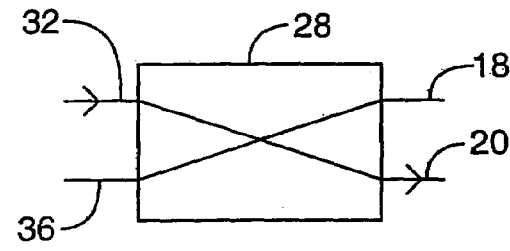
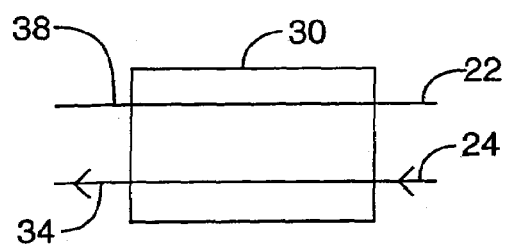
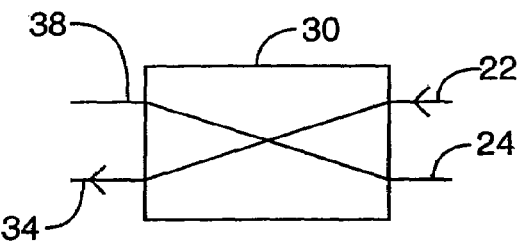
TETRAPOLAR
FIG. 2A  FIG. 2B
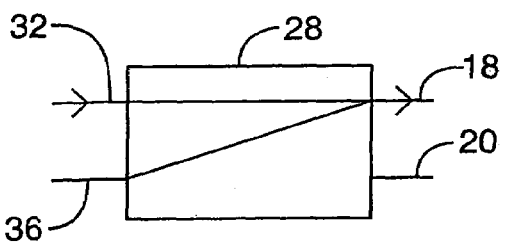
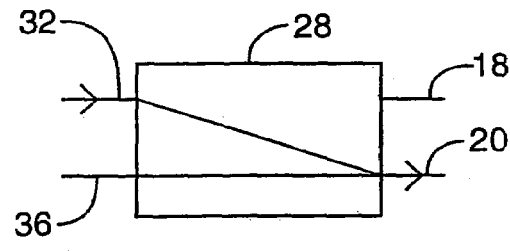
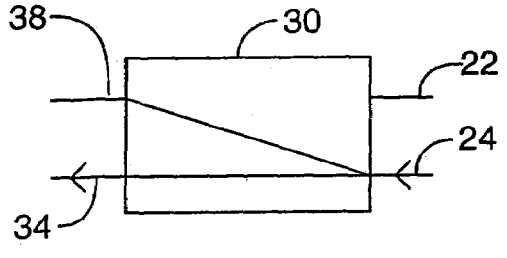
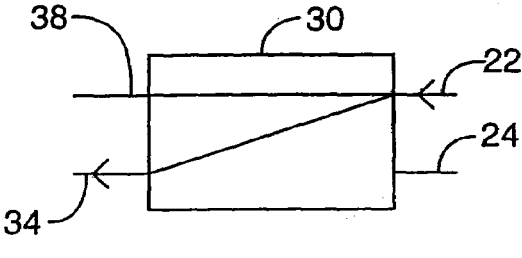
BIPOLAR
FIG. 2C  FIG. 2D

HYBRID

BIOIMPEDANCE MEASUREMENT USING CONTROLLER-SWITCHED CURRENT INJECTION AND MULTIPLEXER SELECTED ELECTRODE CONNECTION

CROSS-REFERENCE TO RELATED APPLICATION

This application claims priority from provisional application Ser. No. 60/429,316 filed Nov. 27, 2002.

FIELD OF THE INVENTION

This invention relates to medical diagnosis of disease and specifically relates to diagnosis of disease using electrical impedances of a body part.

BACKGROUND OF THE INVENTION

The onset of disease is often accompanied by physical changes in a body part. Some physical changes, while not discernible by a patient, can be detected with appropriate diagnostic equipment, often at a relatively early stage of the disease.

For example, the electrical impedances of various body tissues are well known through studies on intact humans or from excised tissue made available following therapeutic surgical procedures. In addition, it is well documented that a decrease in electrical impedance occurs in tissue as it undergoes cancerous changes. This finding is consistent over many animal species and tissue types, including, for example human breast cancers. Consequently, electrical impedance may be used to diagnose disease.

A method that permits comparisons of electrical properties for diagnostic purposes has been developed that involves homologous body parts, i.e., body parts that are substantially similar, such as a left breast and a right breast. In this method, the impedance of a body part of a patient is compared to the impedance of the homologous body part of the same patient. One technique for screening and diagnosing diseased states within the body using electrical impedance is disclosed in U.S. Pat. No. 6,122,544, which is incorporated herein by reference. In this patent, data are obtained from two anatomically homologous body regions, one of which may be affected by disease. Differences in the electrical properties of the two homologous body parts could signal disease.

Published international patent application, PCT/CA01/01788, which is incorporated herein by reference, discloses a breast electrode array for diagnosing the presence of a disease state in a living organism, wherein the electrode array comprises a flexible body, a plurality of flexible arms extending from the body, and a plurality of electrodes provided by the plurality of flexible arms, wherein the electrodes are arranged on the arms to obtain impedance measurements between respective electrodes. In one embodiment, the plurality of flexible arms are spaced around the flexible body and are provided with electrode pairs, which can be used to make tetrapolar impedance measurements.

Tetrapolar impedance measurements are associated with injecting current between so called current injection electrodes and measuring a voltage drop between associated electrodes. In a preferred embodiment, the differences between corresponding homologous impedance measurements in the two body parts are compared in a variety of ways that allows the calculation of metrics that can serve either as an indicator of the presence of disease or to localize the disease to a specific breast quadrant or sector.

The aforementioned system is limited by the number of impedance measurements that can be obtained with the current injection and associated voltage measurement electrodes, and by the fact that only tetrapolar measurements can be performed. Any new system that can yield various types and a greater number of impedance measurements would yield more data that could be processed to make a more accurate diagnosis of disease.

SUMMARY OF THE INVENTION

To find the impedance of a body part, such as a breast, for diagnostic purposes, several electrical measurements are performed with a plurality of electrical leads having electrodes in contact with the skin covering the underlying breast tissue.

Recognizing that the diagnosis of disease can be made more accurate when a large number of impedances are available, the present invention provides a system that can find impedances associated with various electrical pathways in the body part. In addition, the present system can be used to obtain both tetrapolar and bipolar impedance measurements.

In particular, a system and method for measuring a voltage in a body part are described. The system includes a multiplexing unit and N body leads for electrically connecting the multiplexing unit to the body part. The system also includes a controller switching unit for allowing a current to flow through the body part between two body leads, $n_1$ and $n_2$ of the N body leads, and a resultant voltage to be measured between two body leads, $n_3$ and $n_4$ of the N body leads, where $n_1 \neq n_2$ and $n_3 \neq n_4$, but where $n_1$, $n_2$, $n_3$ and $n_4$ need not otherwise be distinct.

In one embodiment, the multiplexing unit includes a multiplexer, and first, second, third and fourth MX leads for connecting the controller switching unit to the multiplexer. The controller switching unit includes a first switch connected to the multiplexer by the first MX lead and the second MX lead, and a second switch connected to the multiplexer by the third MX lead and the fourth MX lead. The controller switching unit further includes a current input lead connected to the first switch for injecting the current into the body part, a current output lead connected to the second switch for receiving the current from the body part, and a first voltage lead connected to the first switch and a second voltage lead connected to the second switch for measuring the resultant voltage. The controller switching unit includes a controller for controlling switch states in the first switch and the second switch, and for controlling multiplexing states in the multiplexer.

The controller switching unit can be in a bipolar mode, corresponding to $n_1 = n_3$ or $n_4$, and $n_2 = n_3$ or $n_4$, or a tetrapolar mode, corresponding to $n_1$, $n_2$, $n_3$ and $n_4$ being all distinct. In the bipolar mode, the current input lead and the first voltage lead are electrically connected to each other and to exactly one of the first MX lead and the second MX lead, and the current output lead and the second voltage lead are electrically connected to each other and to exactly one of the third MX lead and the fourth MX lead. In the tetrapolar mode, the current input lead is electrically connected to exactly one of the first MX lead and the second MX lead and the first voltage lead is electrically connected to the other one of the first MX lead and the second MX lead, and the current output lead is electrically connected to exactly one of the third MX lead and the fourth MX lead and the second voltage lead is electrically connected to the other one of the third MX lead and the fourth MX lead.

The system may further comprise an internal load electrically connected to the first MX lead, the second MX lead, the third MX lead and the fourth MX lead, the internal load used for at least one of internal testing of the system and varying measurement range of the system.

The system may also include an impedance module for generating the current for the input current lead and for measuring the resultant voltage, the impedance module calculating an impedance from the current and the resultant voltage. A diagnosis module can diagnose the possibility of disease in the body part based on the impedance.

Also described herein is a system and method for measuring an electrical property, such as voltage (or other property that can be calculated with the voltage such as a resistance) in a body part. The system includes a multiplexing unit and N body leads for electrically connecting the multiplexing unit to the body part. The system also includes a controller switching unit adapted to allow both bipolar and tetrapolar measurements using the N body leads.

Also described herein is a system and method for measuring an electrical property in a body part. The system includes a multiplexing unit and N body leads for electrically connecting the multiplexing unit to the body part. The system further includes a controller switching unit adapted to allow a) a particular one of the N body leads to inject current into the body part for measuring a first resultant electrical property in a first measurement, and b) the particular one of the N body leads to measure a second resultant electrical property that results from injecting current into the body part in a second measurement. Thus, one lead can be used for injecting current in one measurement, and then used for measuring voltage in a second measurement. Such flexibility allows a greater number of impedance measurements to be performed conveniently.

The present invention describes a system and/or method for measuring an electrical property, such as impedance, in a living tissue that includes a multiplexing unit, body leads and a controller switching unit, which are described in more detail below.

BRIEF DESCRIPTION OF THE DRAWINGS

FIGS. 2A–D shows modes of the controller switching unit of FIG. 1.

DETAILED DESCRIPTION OF THE INVENTION

In an AC circuit, the impedance, Z, is a complex number, whose real part is the resistance R and whose imaginary part is the capacitive reactance $X_C = (\omega C)^{-1}$, where $\omega$ is the frequency at which the voltage (or current) oscillates and C is the capacitance of the circuit. The magnitude of Z is given by $$|Z| = |V/I|,$$

and the phase, $\phi$, of Z is given by $$|\phi| = |\arg(V) - \arg(I)|$$
$$= |\tan^{-1}[X_C(\omega)/R]|,$$

where $I$ denotes the current and V denotes the voltage.

A bioelectrical impedance diagnostic system can be used to measure several impedances of a body part, such as a human breast, to diagnose the possibility of disease therein. The diagnostic system includes various leads that connect to the body part via electrodes. The leads are used to inject current and to measure resultant voltages, which currents and voltages may then be used to calculate impedances. These impedances may then be used for diagnostic purposes because as disease in a body part progresses, the impedance of the body part changes in a predictable fashion. The greater the number of impedances obtained for different electrical pathways, the better the diagnosis can be.

A system is described below that permits the measurement of many impedances with a relatively small number of electrodes. For this purpose, switches are used to increase the number of electrical pathways utilized to measure impedances. The system not only furnishes a greater number of impedances, but also furnishes qualitatively different types of impedances.

Figure 1:
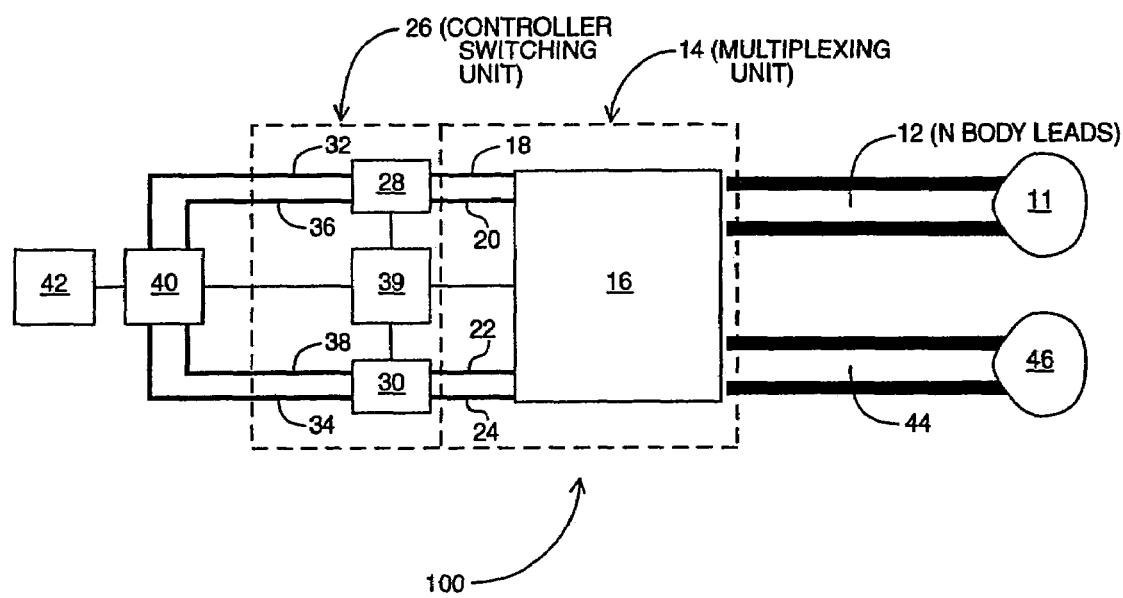
FIG. 1 shows a block diagram of a system for measuring a voltage in a body part, according to the teachings of the present invention.

FIG. 1 shows a system 100 for measuring a voltage in a body part 11, such as a human breast. The system 100 includes N body leads 12. In what follows, the N body leads 12 are ordered from 1 to N for reference. The system 100 also includes a multiplexing unit 14 having a multiplexer 16, a first MX lead 18, a second MX lead 20, a third MX lead 22 and a fourth MX lead 24.

The system 100 further includes a controller switching unit 26 having a first switch 28 connected to the multiplexer 16 by the first MX lead 18 and the second MX lead 20, a second switch 30 connected to the multiplexer 16 by the third MX lead 22 and the fourth MX lead 24, a current input lead 32 connected to the first switch 28, a current output lead 34 connected to the second switch 30, a first voltage lead 36 connected to the first switch 28, and a second voltage lead 38 connected to the second switch 30. The controller switching unit 26 also includes a controller 39. The system 100 further includes an impedance module 40 and a diagnosis module 42.

Also shown in FIG. 1, is an optional second set of leads 44 that can be used when making measurements on a second homologous body part 46. The description below is directed mainly to an impedance measurement on the one body part 11 with the set of N leads 12, but it should be understood that the discussion could be analogously expanded to include an impedance measurement on the second homologous body part 46 with the second set of leads 44. Thus, the principles of the present invention can be applied to diagnosis of disease by making electrical measurements on a single body part, or by making measurements on a homologous pair of body parts. When making measurements on only a single body part, the results can be compared to standard results obtained from population studies, for example, to diagnose disease. When using a homologous pair of body parts, the results of one body part can be compared to the results of the homologous body part of the same patient, as described in U.S. Pat. No. 6,122,544.

The N body leads 12 electrically connect the multiplexing unit 14 to the body part 11. Each of the N body leads 12 includes a wire capable of carrying a current and an electrode to attach to the body part 11. A current conducting gel can act as an interface between the electrode and the skin covering the body part 11.

The multiplexing unit 14 and the controller switching unit 26 allow a current to flow through the body part 11 between any two body leads, $n_1$ and $n_2$, of the N body leads 12, and a resultant voltage to be measured between any two body leads, $n_3$ and $n_4$ of the N body leads 12, where $n_1 \neq n_2$ and $n_3 \neq n_4$, but where $n_1$, $n_2$, $n_3$ and $n_4$ need not otherwise be distinct. Thus, $n_1$, $n_2$, $n_3$, and $n_4$ are numbers belonging to the set $\{1,2, \ldots, N\}$ that identify body leads. For example, if $n_1 = 7$, then $n_1$ denotes the seventh body lead from among the N body leads 12 used to inject current into the body part 11.

The impedance module 40 generates current that is injected into the current input lead 32 and then delivered to the body part. The current output lead 34 receives the current from the body part. When the current is traveling through the body part, the first voltage lead 36 and the second voltage lead 38 are used to measure the resultant voltage between these leads 36 and 38. The impedance module 40 uses this voltage, together with the known current injected into the current input lead 32, to calculate a corresponding impedance, which may then be used by the diagnosis module 42 to diagnose disease.

In one embodiment, N is even and the multiplexer 16 can electrically connect the first MX lead 18 and the fourth MX lead 24 to a first set of N/2 of the N leads, and the second MX lead 20 and the third MX lead 22 to a second set of the other N/2 leads. In a conventional system, the first set of N/2 leads are exclusively used to inject current into and receive current from the body part. The second set of N/2 leads are then exclusively used to measure resultant voltages in tetrapolar measurements. This configuration limits the number of impedances that can be measured.

In the system 100, however, the second set of N/2 leads can also be used to inject and receive current, and the first set can be used to measure resultant voltages. Thus, the system 100 can furnish a greater number of impedances. Moreover, as detailed below, the system can make both tetrapolar and bipolar measurements. The added benefits arise from the functionality of the controller switching unit 26. By using the controller switching unit 26, the system 100 can force current to flow through the body part 11 between any two body leads, $n_1$ and $n_2$, of the N body leads 12, and a resultant voltage to be measured between any two body leads, $n_3$ and $n_4$ of the N body leads 12, where $n_1 \neq n_2$ and $n_3 \neq n_4$.

FIGS. 2A–D show several states of the switches 28 and 30 resulting in different modes of the controller switching unit 26 of the system of FIG. 1. These states of the switches 28 and 30 are controlled by the controller 39. In FIG. 2A, current is injected into the first MX lead 18 and received by the fourth MX lead 24. While this current travels through the body part 11, a resultant voltage is measured between the second MX lead 20 and the third MX lead 22. This measurement is tetrapolar because current is forced to flow between two leads and the resultant voltage is measured between two other leads.

In FIG. 2B, current is injected into the second MX lead 20 and received by the third MX lead 22. The resultant voltage is measured between the first MX lead 18 and the fourth MX lead 24. This measurement is also tetrapolar.

In FIGS. 2A and 2B, the first switch 28 and the second switch 30 are both in tetrapolar states since, for each of the switches 28 and 30, two distinct MX leads are involved in the impedance measurement. When both switch states are tetrapolar, the controller switching unit 26 is said to be in a tetrapolar mode. Thus, FIGS. 2A and 2B correspond to tetrapolar modes.

In a tetrapolar mode, the current input lead 32 is electrically connected to exactly one of the first MX lead 18 and the second MX lead 20 and the first voltage lead 36 is electrically connected to the other one of the first MX lead 18 and the second MX lead 20; likewise, the current output lead 34 is electrically connected to exactly one of the third MX lead 22 and the fourth MX lead 24 and the second voltage lead 38 is connected to the other one of the third MX lead 22 and the fourth MX lead 24.

The two tetrapolar modes shown in FIGS. 2A and 2B do not exhaust all the tetrapolar modes. For example, when the first switch 28 state is the same as the state shown in FIG. 2A and the second switch 30 state is the same as the state shown in FIG. 2B, the controller switching unit 26 is also in a tetrapolar mode. Generally, the controller switching unit 26 is in a tetrapolar mode when $n_1$, $n_2$, $n_3$ and $n_4$ are distinct, where $n_1$ and $n_2$ are leads from among the N leads 12 used to inject current into and receive current from the body part 11, and $n_3$ and $n_4$ are leads used to measure the resultant voltage.

In FIG. 2C, current is injected into the first MX lead 18 and received by the fourth MX lead 24. While this current travels through the body part 11, a resultant voltage is measured between the first MX lead 18 and the fourth MX lead 24. The second and third MX leads 20 and 22 are electrically unconnected to any of the N body leads 12 during this measurement. This measurement is bipolar because the pair of electrodes used for measuring a voltage is also used for current flow.

In FIG. 2D, current is injected into the second MX lead 20 and received by the third MX lead 22. The resultant voltage is measured between the same two leads 20 and 22. The first and fourth MX leads 18 and 24 are electrically unconnected during this measurement. This measurement is also bipolar.

In FIGS. 2C and 2D, the first switch 28 and the second switch 30 are both in bipolar states since, for each of the switches 28 and 30, only one MX lead is involved in the impedance measurement. When both switch states are bipolar, the controller switching unit 26 is said to be in a bipolar mode. Thus, FIGS. 2C and 2D correspond to bipolar modes.

In a bipolar mode, the current input lead 32 and the first voltage lead 36 are electrically connected to each other and to exactly one of the first MX lead 18 and the second MX lead 20, and the current output lead 34 and the second voltage lead 38 are electrically connected to each other and to exactly one of the third MX lead 22 and the fourth MX lead 24.

The two modes shown in FIGS. 2C and 2D do not exhaust all bipolar modes. For example, when the first switch 28 state is the same as the state shown in FIG. 2C and the second switch 30 state is the same as the state shown in FIG. 2D, the controller switching unit 26 is also in a bipolar mode. More generally, the controller switching unit 26 is in a bipolar mode when $n_1 = n_3$ or $n_4$, and $n_2 = n_3$ or $n_4$, where $n_1$ and $n_2$ are leads from among the N leads 12 used to inject and receive current, and $n_3$ and $n_4$ are leads used to measure the resultant voltage.

Figure 3:
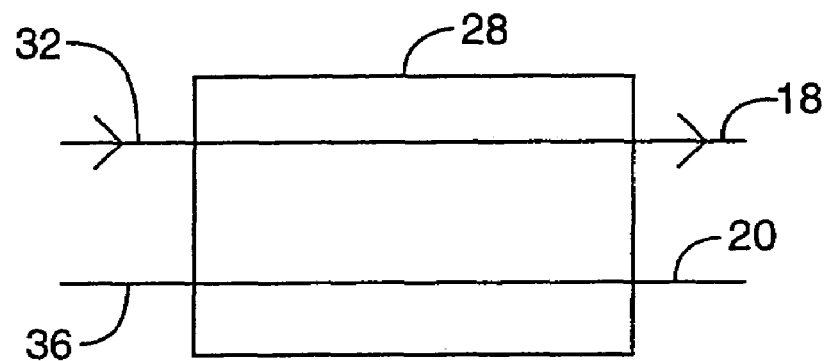
FIG. 3 shows a hybrid mode of the controller switching unit of FIG. 1.
Figure 3:
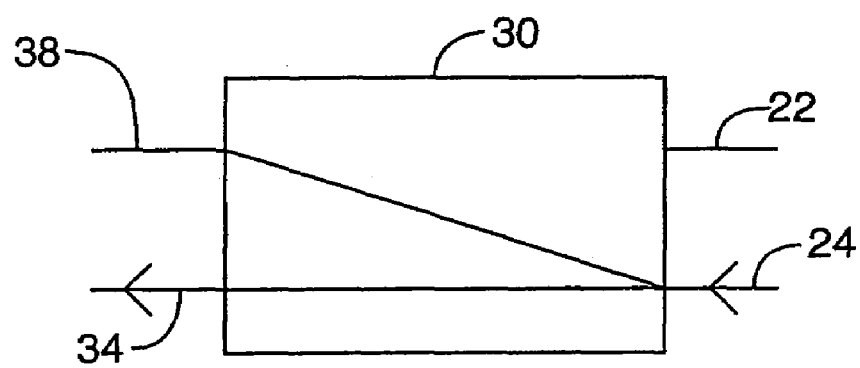

In addition to the tetrapolar and bipolar modes shown in FIGS. 2A–2D, there are also hybrid modes. FIG. 3 shows a hybrid mode of the controller switching unit 26 of FIG. 1. Here, the first switch 28 is in a tetrapolar state and the second switch 30 is in a bipolar state. In a hybrid mode, $n_1 \neq n_3$ and $n_2 = n_4$, or $n_1 \neq n_4$ and $n_2 = n_3$, where again $n_1$ and $n_2$ are used for current flow and $n_3$ and $n_4$ are used for voltage measurement.

In FIG. 3, the lead $n_1$ is electrically connected to the first MX lead 18 or to the fourth MX lead 24 via the multiplexer 16. The lead $n_2$ is connected to whichever of first MX lead 18 and the fourth MX lead 24 is not connected to the lead $n_1$. The lead $n_3$ is connected to the second MX lead 20 or the fourth MX lead 24, and the lead $n_4$ is connected to whichever of the second MX lead 20 and the fourth MX lead 24 is not connected to the $n_3$ lead. The third MX lead 22 is electrically unconnected during this hybrid measurement.

Figure 4:
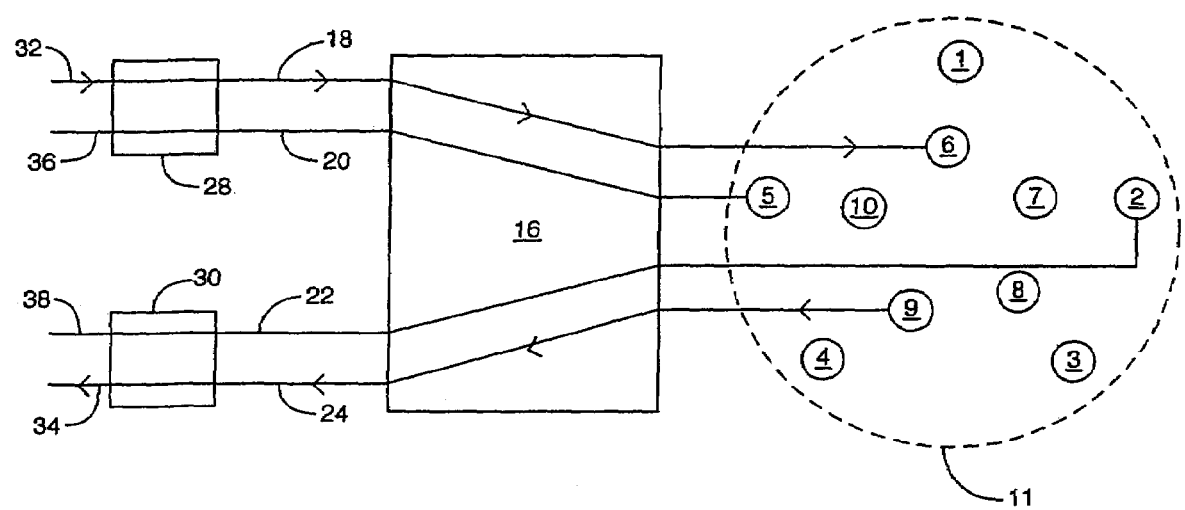
FIG. 4 shows electrical connections in a particular tetrapolar impedance measurement that employs the system of FIG. 1.

FIG. 4 shows electrical connections in a particular tetrapolar impedance measurement that employs the system 100 of FIG. 1. For simplicity, the system 100 has only N=10 leads, and the controller 39, the impedance module 40 and the diagnosis module 42 are not shown. In a different embodiment, N=32. Also not shown in the FIG. 4 is the second set of leads 44. The ten electrodes of the ten leads are shown: the first set of N/2=five electrodes 1–5 lie on the outside perimeter and the other set of five electrodes 6–10 lie on the inner perimeter.

All the electrodes 1–5 of the first set can be electrically connected to the first and fourth MX leads 18 and 24, and all the electrodes 6–10 of the second set can be connected to the second and third MX leads 20 and 22 via the multiplexer 16. In the example of FIG. 4, the connections shown are for one tetrapolar measurement in which $n_1=6$, $n_2=9$, $n_3=2$ and $n_4=5$, where electrode 6 is used to inject current into the body part 11 and electrode 9 is used to receive the current. The electrodes 2 and 5 are used to measure the resultant voltage. Although all electrodes of the ten leads are shown in FIG. 4, only the four wires of the electrically active leads appear.

In particular, current is generated by the impedance module 40 and sent to the current input lead 32. From there, the current travels to the first MX lead 18 via the first switch 28 and from there to the electrode 6 via the multiplexer 16. The current next travels through the body part 11 to the electrode 9 and then through the multiplexer 16 to the fourth MX lead 24. The current then flows to the current output lead 34 via the second switch 30 and then back to the impedance module 40. The resultant voltage is measured between the first and second voltage leads 36 and 38, which corresponds to the voltage between the electrodes 2 and 5. The first voltage lead 36 is connected to the electrode 2 via the first switch 28 and the multiplexer 16, and the second voltage lead 38 is electrically connected to the electrode 5 via the second switch 30 and the multiplexer 16. The controller 39 controls the states of the switches 28 and 30 and the multiplexing states in the multiplexer 16 that determine through which leads current flows and which leads are used to measure voltage.

Figure 5A:
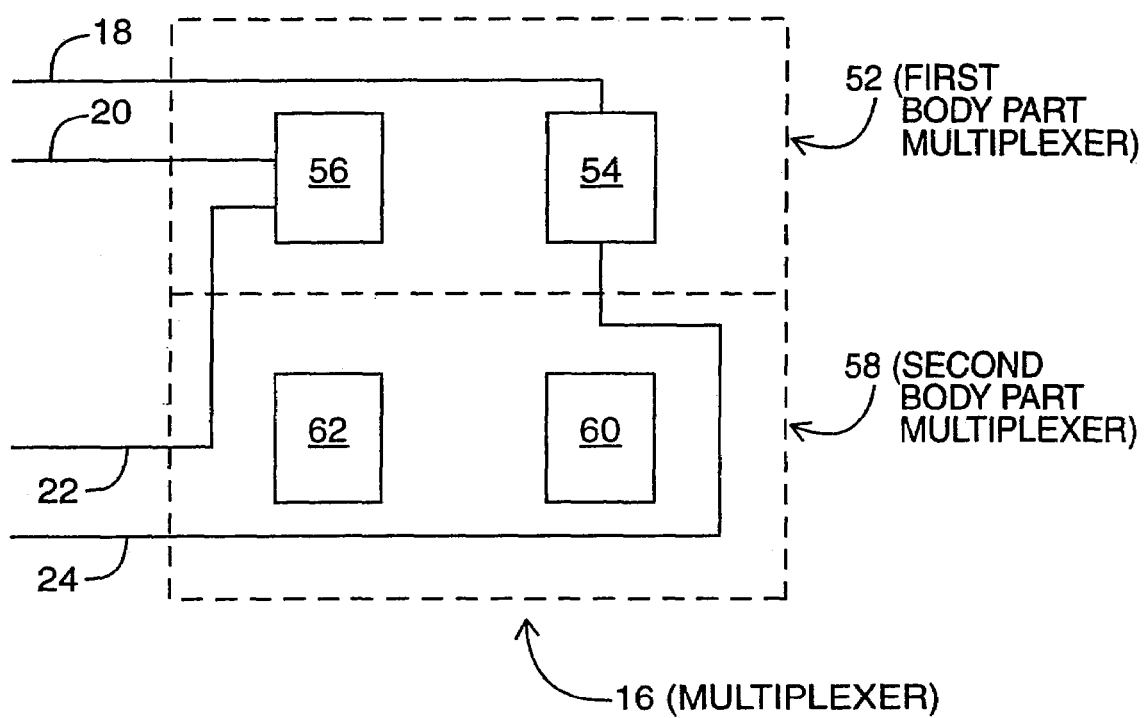
FIGS. 5A and 5B show the multiplexer of FIG. 1.

FIG. 5A shows the multiplexer 16 of FIG. 1 in an embodiment in which a body part is being compared to a homologous body part. The multiplexer 16 includes a first body part multiplexer 52 that includes a first body part A multiplexer unit 54 and a first body part B multiplexer unit 56. The multiplexer 16 also includes a second body part multiplexer 58 that includes a second body part A multiplexer unit 60 and a second body part B multiplexer unit 62. The first body part A multiplexer unit 54 is connected to the first MX lead 18 and the fourth MX lead 24. The first body part B multiplexer unit 56 is connected to the second MX lead 20 and the third MX lead 22. Although not shown in the interest of clarity, the second body part A multiplexer unit 60 is also connected to the first MX lead 18 and the fourth MX lead 24, and the second body part B multiplexer unit 62 is also connected to the second MX lead 20 and the third MX lead 22.

The first body part multiplexer 52 is used for multiplexing electrical signals to the first body part of the homologous pair. In particular, the first body part A multiplexer unit 54 and B multiplexer unit 56 are both capable of multiplexing current and voltage signals to and from the N leads 12. Likewise, the second body part multiplexer 58 is used for multiplexing electrical signals to the homologous body part. In particular, the second body part A multiplexer unit 60 and B multiplexer unit 62 are both capable of multiplexing current and voltage signals to and from the N leads 12, as described below.

Figure 5B:
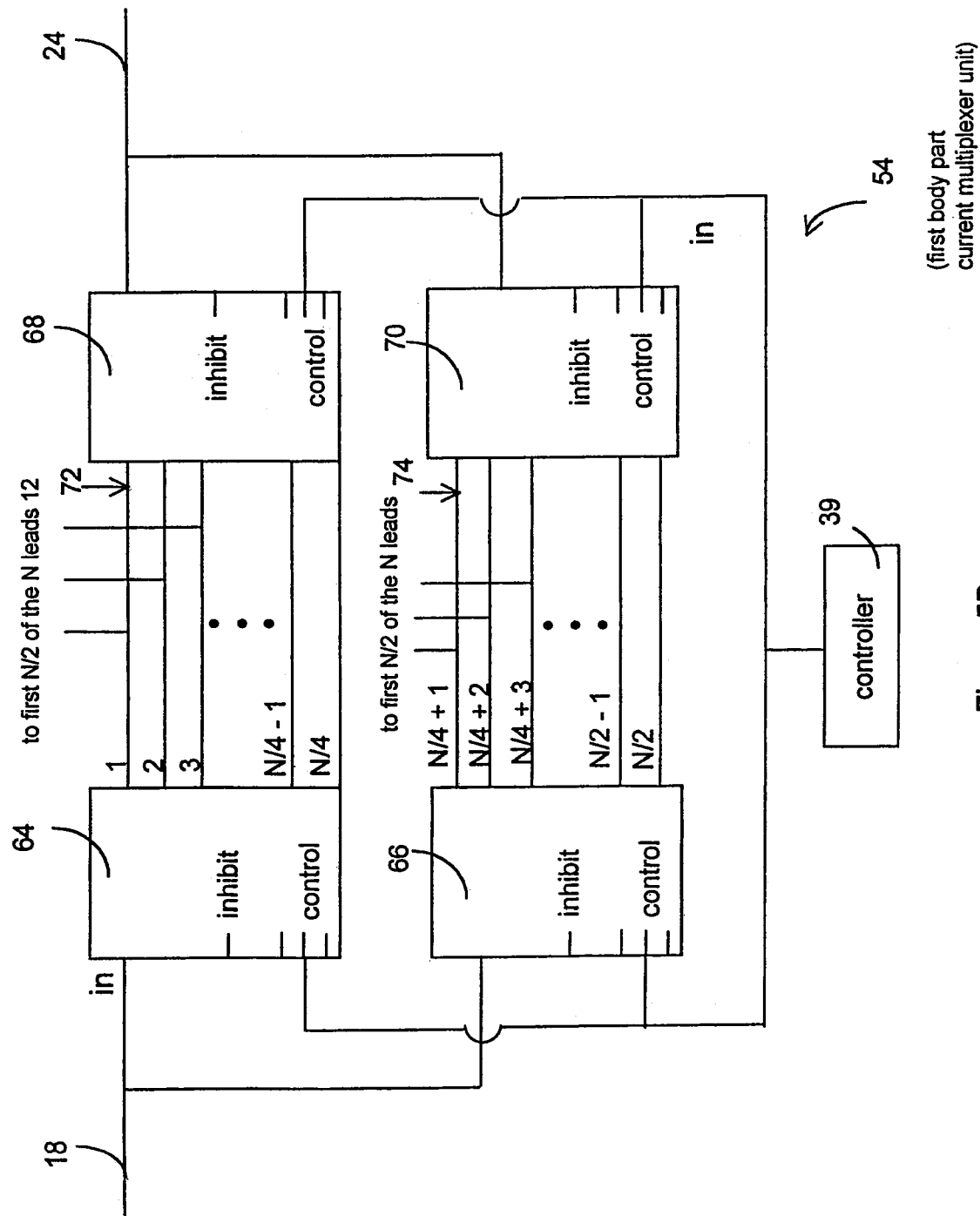

FIG. 5B shows the first body part A multiplexer unit 54 of FIG. 5A. The multiplexer unit 54 includes four one-to-N/4 multiplexers 64, 66, 68 and 70. These, for example, can be model number MAX4051ACPE manufactured by MAXIM™. The N/4 multiplexer current leads 72 connect the multiplexer 64 to the multiplexer 68, and N/4 multiplexer current leads 74 connect the multiplexers 66 and 70. In turn, the leads 72 and 74 are connected to the first N/2 of the N leads 12. The multiplexers 64, 66, 68 and 70 each have a configurable one bit "inhibit state" and $\log_2(N/4)$ bit "control state." The inhibit state can be either off (0) or on (1) and determines whether current can flow through the respective multiplexer 64, 66, 68 or 70. The control state determines through which one of the leads 72, 74 current flows. If N=32, then four bits are required for each active multiplexer (by "active" is meant that the inhibit state is off) and to specify a state, one for the inhibit state and three for the control state. For example, if the inhibit state of the multiplexer 64 is 1 (on) and the state of the multiplexer 66 is (0,1,0,0), where the first bit is for the inhibit state, then current destined for the breast is directed to the tenth lead, provided the states of the switches 28 and 30 connect the current input lead 32 to the first MX lead 18, as previously described. If the states of the switches 28 and 30 do not connect the current input lead 32 to the first MX lead 18, but do connect the first voltage lead 36 to the first MX lead 18, then this lead 18, when the multiplexer 66 is in the state (0,1,0,0), measures the resultant voltage with the tenth lead.

A similar binary code for the multiplexers 68 and 70 dictates through which one of the first 16 electrodes of the 32 leads 12 current is received from the breast, provided the states of the switches 28 and 30 connect the current output lead 34 to the fourth MX lead 24. If the fourth MX lead 24 is not connected to the current output lead 34, but is connected to the second voltage lead 22, then the fourth MX lead 24 is used for measuring the resultant voltage, provided the inhibit state of the multiplexer 68 or the multiplexer 70 is off.

The B multiplexer unit 56 is similar to the A multiplexer unit 54 in that it has four one-to-N/4 multiplexers analogous to 64, 66, 68 and 70. However, the one-to-N/4 multiplexers are capable of connecting with the second and third MX leads 20 and 22, instead of the first and fourth MX leads 18 and 24. Here, the inhibit and control states determine which electrode from among the other N/2 electrodes is used to deliver current or measure voltage.

Thus, by setting inhibit and control states, in coordination with the states of the switches 28 and 30, it is possible to direct current between any pair of the N leads 12 and to make a measurement of the resultant voltage between any pair of the N leads 12.

The inhibit and control states are set by the controller 39 with a shift-register and/or a computer. A direct digital stream can be sent to the shift register for this purpose.

The function of the second body part multiplexer 58 is analogous to that of the first body part multiplexer 52 and therefore need not be described further.

Figure 6:
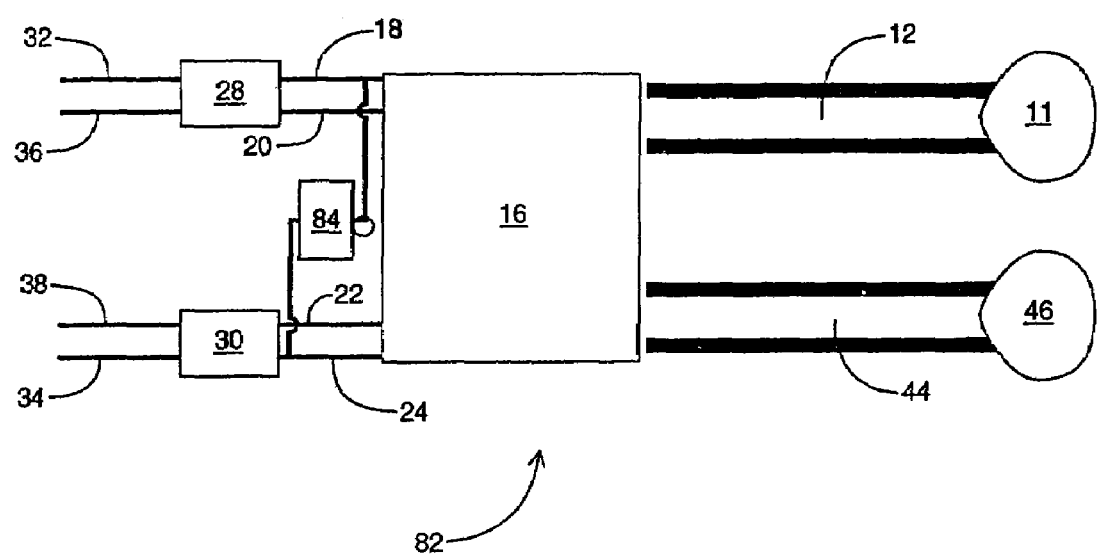
FIG. 6 shows a diagnostic system that includes an internal load in addition to the components of FIG. 1.

FIG. 6 shows a diagnostic system 82 that includes an internal load 84 in addition to the components described above in relation to FIG. 1. The internal load 84 is electrically connected to the first MX lead 18, the second MX lead 20, the third MX lead 22 and the fourth MX lead 24. The internal load 84 is used for at least one of internal testing of the system 82 and varying the measurement range of the system 82.

Using the first switch 28 and the second switch 30, the internal load 84 can be connected to the impedance module 40 in a tetrapolar mode or in a bipolar mode. The internal load 84 has a known impedance and therefore can be used to test the diagnostic system 82.

Additionally, the internal load 84 can be used to change the measurement range of the system 82. By attaching this internal load 84 in parallel with any load, such as the body part 11, the system 82 is capable of measuring larger impedances than would otherwise be possible. If the resistance of the internal load 84 is $R_{int}$ and is in parallel, the measured resistance R is given by $$R=(1/R_{load}+1/R_{int})^{-1}$$

where $R_{load}$ is the resistance of the load. Consequently, the measured resistance is reduced from the value without the internal load, thereby increasing the measurement range of the system 84.

Figure 7:
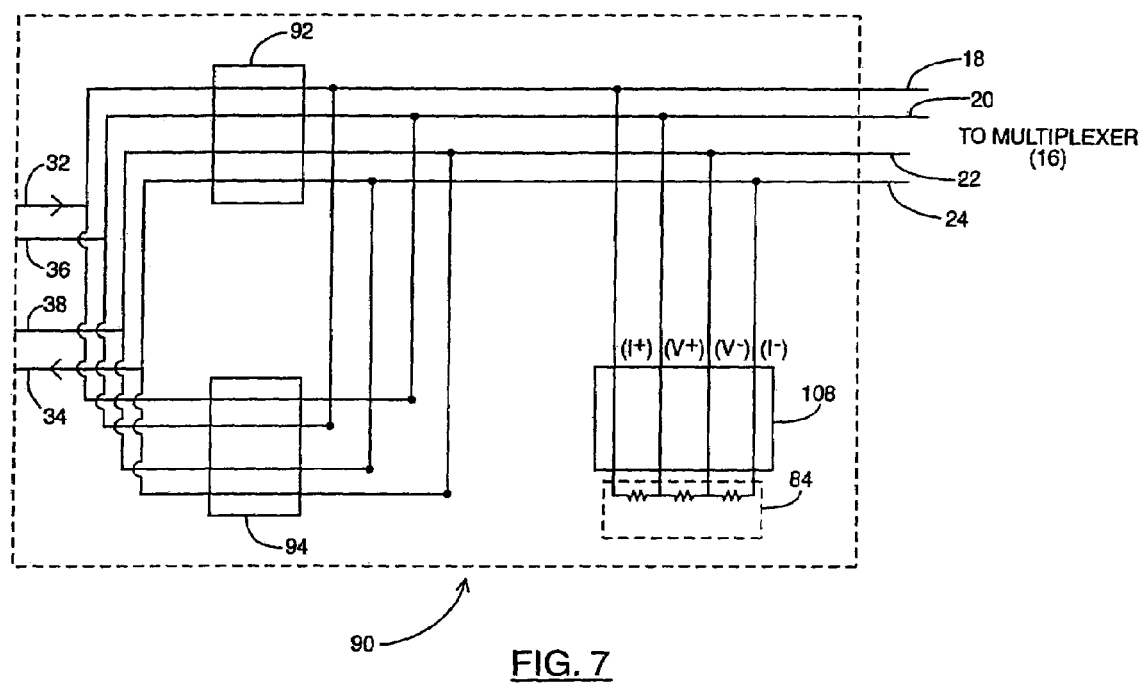
FIG. 7 shows one embodiment of the controller switching unit, according to the principles of the present invention.

The switches 28 and 30 allow current to flow between various pairs of electrodes on a body part, and resultant voltage to be measured between various pairs of electrodes, as described above with reference to FIGS. 1–6. In FIG. 7, another embodiment of the controller switching unit is shown that can be used to achieve the states of FIG. 2 using a different electrical circuit topology. The controller switching unit 90 of FIG. 7 includes a first switch 92 and a second switch 94. The current input lead 32, the current output lead 34, the first voltage lead 36 and the second voltage lead 38 split to connect to both the first and second switches 92 and 94.

The switches 92 and 94 can be turned on or off and can be used to make tetrapolar and bipolar measurements. With only one of the switches 92 and 94 on, a tetrapolar measurement can be made. With both switches 92 and 94 on, a bipolar measurement can be made. For example, when the first switch 92 is on, and the second switch is off, the resultant functionality corresponds to that of FIG. 2A, albeit achieved with a different circuit topology. In this example, current flows from the impedance module 40 along the current input lead 32, through the first switch 92, and then to the first MX lead 18. From there, the current proceeds to the multiplexer 16. Current is received from the multiplexer 16 along the fourth MX lead, and delivered to the current output lead 34 via the first switch 92. The resultant voltage is measured between the second and third MX leads 20 and 22 with the use of the first and second voltage leads 36 and 38.

In another example, when the first switch 92 is off, and the second switch 94 is on, the resultant functionality corresponds to that of FIG. 2B. Here, current from the impedance module 40 travels along the current input lead 32, across the second switch 94, then jumps to the second MX lead 20. Current is received along the third MX lead 22, from where it jumps to the current output lead 34 via the second switch 94. The voltage is measured between the first and fourth MX leads 18 and 24 with the use of the first and second voltage leads 36 and 38.

In yet another example, the first and second switches 92 and 94 are both on, which corresponds to FIG. 2C or 2D. Precisely to which of these two figures this example corresponds is determined by the inhibit states of the multiplexer 16. For example, if the inhibit states of both of the one-to-N/4 multiplexers 64 and 66 are on, then bipolar measurements are performed with the second set of N/2 electrodes.

The controller switching unit 90 also includes an internal load switch 108 that is connected to the internal load 84. The controller switching unit 90 and the internal load 84 are used to test the system and to increase the measurement range, as described above.

It should be understood that various modifications could be made to the embodiments described and illustrated herein, without departing from the present invention, the scope of which is defined in the appended claims. The present invention involves the use of an electrode array for measuring impedances of a breast to determine the condition thereof. However, although emphasis has been placed on describing a system for diagnosing breast cancer, the principles of the present invention can also be advantageously applied to other diseases of other body parts. In addition, the principles of the present invention can be applied to measurements on a single body part, or on two homologous body parts.

What is claimed is:

1. A system for measuring a voltage in a body part, the system comprising
   a multiplexing unit;
   N body leads for electrically connecting the multiplexing unit to the body part;
   an impedance module for generating a current and for measuring a resultant voltage, the impedance module calculating an impedance from the current and the resultant voltage;
   a controller switching unit electrically connecting the impedance module to the multiplexing unit, the controller switching unit having a first switch connected to the multiplexer and at least a second switch connected to the multiplexer to allow the current to flow through the body part between two body leads, $n_1$ and $n_2$ of the N body leads, and the resultant voltage to be measured between two body leads, $n_3$ and $n_4$ of the N body leads, where $n_1 \neq n_2$ and $n_3 \neq n_4$, but where $n_1$ $n_2$ $n_3$ and $n_4$ need not otherwise be distinct;
   a current input lead connected to the first switch for injecting the current into the body part;
   a current output lead connected to the second switch for receiving the current from the body part; and
   a first voltage lead connected to the first switch and a second voltage lead connected to the second switch for measuring the resultant voltage.

2. The system of claim 1, wherein the multiplexing unit includes
   a multiplexer; and
   a first MX lead, a second MX lead, a third MX lead and a fourth MX lead for connecting the controller switching unit to the multiplexer.

3. The system of claim 2, wherein
the first switch is connected to the multiplexer by the first MX lead and the second MX lead; and
the second switch is connected to the multiplexer by the third MX lead and the fourth MX lead.

4. The system of claim 3, wherein the controller switching unit can be in a bipolar mode, corresponding to $n_1=n_3$ or $n_4$, and $n_2=n_3$ or $n_4$, or a tetrapolar mode, corresponding to $n_1$, $n_2$, $n_3$ and $n_4$ being all distinct.

5. The system of claim 4, wherein, in the bipolar mode, the current input lead and the first voltage lead are electrically connected to each other and to exactly one of the first MX lead and the second MX lead, and the current output lead and the second voltage lead are electrically connected to each other and to exactly one of the third MX lead and the fourth MX lead.

6. The system of claim 4, wherein, in the tetrapolar mode, the current input lead is electrically connected to exactly one of the first MX lead and the second MX lead and the first voltage lead is electrically connected to the other one of the first MX lead and the second MX lead, and the current output lead is electrically connected to exactly one of the third MX lead and the fourth MX lead and the second voltage lead is electrically connected to the other one of the third MX lead and the fourth MX lead.

7. The system of claim 3, further comprising an internal load electrically connected to the first MX lead, the second MX lead, the third MX lead and the fourth MX lead, the internal load used for at least one of internal testing of the system and varying measurement range of the system.

8. The system of claim 1, wherein the controller switching unit includes a controller for controlling switch states in the first switch and the second switch, and for controlling multiplexing states in the multiplexer.

9. The system of claim 1, wherein the body part is a breast.

10. The system of claim 1, further comprising a diagnosis module for diagnosing the possibility of disease in the body part based on the impedance.

11. A method for measuring a voltage in a body part, the method comprising
providing a multiplexing unit;
connecting the body part to the multiplexing unit with N body leads;
generating a current with an impedance module;
electrically connecting the multiplexer to a first switch in a controller switching unit;
electrically connecting the multiplexer to a second switch in the controller switching unit;
injecting current into the body part with a current input lead that is connected to the first switch so that current is sent by the multiplexer between two body leads, $n_1$ and $n_2$ of the N body leads in response to control signals sent by the controller switching unit;
receiving the current from the body part with a current output lead that is connected to the second switch;
measuring a resultant voltage between two body leads, $n_3$ and $n_4$ of the N body leads, where $n_1 \neq n_2$ and $n_3 \neq n_4$, but where $n_1$ $n_2$ $n_3$ and $n_4$ need not otherwise be distinct, the resultant voltage measured with a first voltage lead connected to the first switch and a second voltage lead connected to the second switch;
measuring the resultant voltage with the impedance module; and
calculating an impedance from the current and the resultant voltage.

12. The method of claim 11, the method further comprising
electrically connecting the controller switching unit to the multiplexer with a first MX lead, a second MX lead, a third MX lead and a fourth MX lead.

13. The method of claim 12, further comprising
electrically connecting the multiplexer to the first switch in the controller switching unit with the first MX lead and the second MX lead; and
electrically connecting the multiplexer to the second switch in the controller switching unit with the third MX lead and the fourth MX lead.

14. The method of claim 13, further comprising placing the controller switching unit in a bipolar mode, corresponding to $n_1=n_3$ or $n_4$, and $n_2=n_3$ or $n_4$, or a tetrapolar mode, corresponding to $n_1$, $n_2$, $n_3$ and $n_4$ all being distinct.

15. The method of claim 14, wherein the step of placing the controller switching unit in a bipolar mode includes
electrically connecting the current input lead and the first voltage lead to each other and to exactly one of the first MX lead and the second MX lead; and
electrically connecting the current output lead and the second voltage lead to each other and to exactly one of the third MX lead and the fourth MX lead.

16. The method of claim 15, wherein the step of placing the controller switching unit in a tetrapolar mode includes
electrically connecting the current input lead to exactly one of the first MX lead and the second MX lead;
electrically connecting the first voltage lead to the other one of the first MX lead and the second MX lead;
electrically connecting the current output lead to exactly one of the third MX lead and the fourth MX lead; and
electrically connecting the second voltage lead to the other one of the third MX lead and the fourth MX lead.

17. The method of claim 13, further comprising providing an internal load electrically connected to the first MX lead, the second MX lead, the third MX lead and the fourth MX lead; and
using the internal load used for at least one of internal testing of the system and varying measurement range of the system.

18. The method of claim 11, wherein the body part is a breast.

19. The method of claim 11 further comprising diagnosing the possibility of disease in the body part based on the impedance.

* * * * *